United States Patent [19]

Calderon

[11] 3,935,270

[45] *Jan. 27, 1976

[54] PROCESS FOR THE PREPARATION OF CYCLOHEXADECENONES AND DERIVATIVES

[75] Inventor: Nissim Calderon, Akron, Ohio

[73] Assignee: The Goodyear Tire & Rubber Company, Akron, Ohio

[ * ] Notice: The portion of the term of this patent subsequent to Apr. 15, 1986, has been disclaimed.

[22] Filed: Feb. 23, 1968

[21] Appl. No.: 707,486

Related U.S. Application Data

[63] Continuation-in-part of Ser. No. 664,907, Sept. 1, 1967, Pat. No. 3,439,056.

[52] U.S. Cl. .... 260/586 P; 260/348 C; 260/348.52; 260/457; 260/586 M; 260/606.5 B; 260/617 M; 260/648 R; 260/666 A
[51] Int. Cl.².......................................... C07C 45/04
[58] Field of Search......... 260/586 A, 586 P, 586 M

[56] References Cited
UNITED STATES PATENTS

| | | |
|---|---|---|
| 3,235,601 | 2/1966 | Parson et al. ........................ 260/586 |
| 3,365,499 | 1/1968 | Clement et al. ................. 260/587 X |
| 3,370,073 | 2/1968 | Clement et al. ................. 260/587 X |
| 3,560,591 | 2/1971 | Kropp ............................. 260/587 X |

OTHER PUBLICATIONS

Mathur et al., Chemical Abstracts, Vol. 63, p. 8221 b, [1965].

*Primary Examiner*—Norman Morgenstern
*Attorney, Agent, or Firm*—F. W. Brunner; J. Y. Clowney

[57] ABSTRACT

A method for the preparation of alicyclic ketones containing 16 carbon atoms in the ring which comprises converting an alicyclic compound possessing 8 carbon atoms in the unsaturated ring such as cyclooctenes and cyclooctadienes into alicyclic compounds which contain 16 carbon atoms in the ring and containing at least 2 carbon-to-carbon double bonds and subsequently converting at least one of the double bonds in such a compound into a carbonyl or ketone functional group is disclosed.

4 Claims, No Drawings

PROCESS FOR THE PREPARATION OF CYCLOHEXADECENONES AND DERIVATIVES

This application is a continuation-in-part of application Ser. No. 664,907, filed Sept. 1, 1967, entitled "Macrocyclic Compounds Preparation" now U.S. Pat. No. 3,439,056, issued Apr. 15, 1969.

An aspect of this invention relates to novel methods of preparation of large ring alicyclic ketones. Another aspect concerns processes which convert medium-sized unsaturated alicyclic hydrocarbons into alicyclic ketones which contain a larger number of carbon atoms in the skeleton of the alicyclic ring.

It is well known that macrocyclic ketones such as muscone (3-methylcyclopentadecanone), civetone (9-cycloheptadecenone-1), dihydrocivetone (cycloheptadecanone) and exaltone (cyclopentadecanone) are extremely valuable as perfume bases because they exhibit a pleasant and lasting musk odor. Most of the macrocyclic ketones used as perfume base are extracted from natural sources such as the glands of muskrats and civet cats and, therefore, are extremely expensive.

It is an object of this invention to provide a method whereby cyclic ketones containing 16 carbon atoms in the alicyclic rings may be made synthetically. Another object is to provide an economical process to produce cyclic ketones containing 16 carbon atoms in the alicyclic ring. Still another object is to provide a method whereby the cyclic ketones containing about 16 carbon atoms in the alicyclic ring can be produced from relatively simple starting materials. Another object is to provide a simple and less complex method than that heretofore known to provide cyclic ketones containing 16 carbon atoms in the alicyclic ring. Other objects will appear as the description proceeds.

According, these and other objects are accomplished by converting an alicyclic compound possessing 8 carbons in the unsaturated ring, selected from the group of cyclooctenes, alkyl substituted cyclooctenes, cyclooctadienes and alkyl substituted cyclooctadienes into alicyclic compounds which contain 16 carbon atoms in the alicyclic ring and contain at least two carbon-to-carbon double bonds in the ring and subsequently converting at least one of the double bonds in the said compound into a ketone functional group.

According to the invention, at least one member selected from the group of cyclooctene, cyclooctadiene, alkyl substituted cyclooctenes and alkyl substituted cyclooctadienes is subjected to a catalyst comprising (A) at least one organometallic compound wherein the metal is selected from the group consisting of Ia, IIa, IIb and IIIa groups of the Periodic Table of Elements, (B) at least one metal salt wherein the metal is selected from the group consisting of molybdenum and tungsten, and (C) at least one compound of the general formula R—Y—H wherein Y is selected from the group of oxygen and sulfur and wherein R is a radical selected from the group consisting of (1) hydrogen, (2) alkyl, (3) aryl, (4) arylalkyl, (5) alkaryl, (6) alkenyl, (7) when Y is S, R is thioalkyl, thioarylalkyl and thioalkaryl, (8) when Y is O, R is alkoxy, arylalkoxy and alkaryloxy and radicals of (2) through (6) wherein at least one hydrogen is substituted by a material selected from hydroxyl (OH) and thiol (SH) groups, to form at least one material selected from the group consisting of cyclohexadecadiene, alkyl substituted cyclohexadecadiene, cyclohexadecatetraene and alkyl substituted cyclohexadecatetraene and subsequently converting at least one double bond of such materials to the corresponding ketone group.

According to the invention an alicyclic compound precursor corresponding to the formula

wherein
1. Q comprises a sequence of six carbon atoms situated in linear succession between the methylidene carbons which constitute the double bond;
2. the carbon atoms in the linear succession of Q may be interconnected by either carbon-carbon single bonds or carbon-carbon double bonds;
3. any of the carbon atoms in the linear succession of Q may be substituted by alkyl radicals; and
4. said alicyclic compounds containing no conjugated double bonds, is converted into at least one macrocyclic compound possessing alicyclic unsaturated ring containing 16 carbon atoms and containing at least two carbon to carbon double bonds, subsequently converting at least one of said double bonds in said alicyclic rings to a ketone functional group.

As previously indicated, it is possible to prepare large ring unsaturated alicyclic compounds from smaller unsaturated alicyclic precursors. These alicyclic compounds which contain 8 or more carbon atoms are cycloolefins, which polymerize by a ring opening mechanism forming polymers containing carbon to carbon unsaturation along the polymer chains may undergo simultaneously an intramolecular olefin metathesis process leading to the formation of large ring unsaturated alicyclic compounds. It has been discovered that the ring opening polymerization of these medium-size unsaturated, alicyclic monomers can be modified substantially to form larger unsaturated, alicyclic compounds by conducting the reaction in high dilutions. One may adjust the reaction conditions by employing sufficient amounts of diluent which lead to the enhancement of the intramolecular mode of reaction, thus, obtaining a high proportion of the large ring unsaturated alicyclic compounds. A dilution of about 10% or more of the unsaturated alicyclic compounds in an inert diluent will usually cause the mode of reaction to be intramolecular and form high proportions of the large ring unsaturated alicyclic compounds. However, a dilution to about 5% or more of the alicyclic unsaturated molecules in the inert diluent is more preferable. Suitable diluents for this purpose are liquids which do not adversely affect the catalyst activity or the olefin metathesis reaction. Representative of such diluents are saturated hydrocarbons such as butane, pentane, heptane, hexane and the like or aromatic hydrocarbons such as benzene, toluene and the like. Hydrocarbons which contain other substituents may also be employed provided that they are inert.

The product mixture of these large ring alicyclic compounds can be conveniently separated from any high molecular weight polymer which may be formed due to the intermolecular mode of reaction from the ring opening polymerization of these alicyclic compounds by extraction with a choice of suitable solvents. The separation of the mixture of the large ring unsaturated alicyclic compounds to its individual components according to ring sizes can be accomplished by one skilled in the art by using a choice of methods. Such known methods would be fractional distillations at reduce pressures, molecular distillations, elution chromatography, vapor phase chromatography and gel permeation chromatography.

The alicyclic compounds useful in the preparation of the products of this invention are those containing 8 or more carbon atoms. Representative of such alicyclic compounds are cyclooctene, 1,4- and 1,5-cyclooctadiene and alkyl substituted cyclooctene and alkyl substituted 1,4- and 1,5-cyclooctadiene such as methyl cyclooctenes, ethyl cyclooctenes, methyl cyclooctadienes, ethyl cyclooctadienes and other alkyl substituted cyclooctenes and cyclooctadienes.

The conversion of the alicyclic compounds which are the starting materials of this invention to form the large ring alicyclic unsaturated hydrocarbons containing at least 16 carbon atoms in the ring is conducted in the presence of a catalyst system which will cause these reactions to take place.

A class of catalysts employed in the macrocyclization reaction of this invention is a combination comprising (A) at least one organometallic compound wherein the metal is selected from the group consisting of Ia, IIa, IIb and IIIa groups of the Periodic Table of Elements, (B) at least one metal salt wherein the metal is selected from the group consisting of molybdenum and tungsten, and (C) at least one compound of the general formula R—Y—H wherein Y is selected from the group of oxygen and sulfur and wherein R is a radical selected from the group consisting of (1) hydrogen, (2) alkyl, (3) aryl, (4) arylalkyl, (5) alkaryl, (6) alkenyl, (7) when Y is S, R is thioalkyl, thioarylalkyl and thioalkaryl, (8) when Y is O, R is alkoxy, arylalkoxy and alkaryloxy and radicals of (2) through (6) wherein at least one hydrogen is substituted by a material selected from hydroxyl (OH) and thiol (SH) groups. The Periodic Table of Elements referred to may be found in the Handbook of Chemistry and Physics, 44th Edition, April, 1962 reprint, published by the Chemical Rubber Publication Company, Cleveland, Ohia, U.S.A., pg. 448.

Representative examples of metals from which the organometallic compound, the first or (A) component of the catalyst system of this invention, can be derived are lithium, sodium, potassium, rubidium, cesium, beryllium, magnesium, calcium, strontium, barium, zinc, cadmium, aluminum, gallium, indium, and thallium. The preferred organometallic compounds are compounds of lithium, sodium, magnesium, aluminum, zinc and cadmium with aluminum being most preferred.

Representative examples or organometallic compounds useful as the first or (A) catalyst component of this invention are aluminum compounds having at least one metal-to-carbon bond. Representative of such compounds are trialkylaluminums such as trimethylaluminum, triethylaluminum, tri-n-propylaluminum, tri-n-butylaluminum, triisopropylaluminum, triisobutylaluminum, trihexylaluminum, trioctylaluminum and the like; triarylaluminums such as tritolylaluminum, tribenzylaluminum, triphenylaluminum and the like; dialkylaluminum halides such as diethylaluminum chloride, di-n-propylaluminum chloride, diisobutylaluminum chloride, diethylaluminum bromide, diethylaluminum iodide and diethylaluminum fluoride and the like; mixtures of dialkylaluminum halides and alkylaluminum dihalides such as ethylaluminum sesquichloride and bromides may also be employed; alkylaluminum dihalides such as ethylaluminum dichloride, ethylaluminum dibromide, propylaluminum dichloride, isobutylaluminum dichloride, ethylaluminum diiodide and the like; dialkylaluminum hydrides such as diethylaluminum hydride, di-n-propylaluminum hydride, diisobutylaluminum hydride and the like; arylaluminum hydrides and dihydrides such as diphenylaluminum hydride and phenylaluminum dihydride, the arylaluminum halides such as phenylaluminum dibromide, tolylaluminum dibromide, benzylaluminum dibromide, phenylaluminum diiodide, tolylaluminum diiodide, benzylaluminum diiodide, diphenylaluminum chloride, ditolylaluminum chloride, dibenzylaluminum bromide and the like. Other organometallic compounds are also useful in the practice of this invention. Representative of such organometallic compounds are organoalkali metal compounds such alkyllithium compounds as ethyllithium, n-butyllithium, t-butyllithium, and the like; lithium-aluminum-tetraalkyls such as lithium-aluminum-tetrabutyl, lithium-aluminum-tetraethyl and the like; alkali metal alkyls and aryls such as amylsodium, butylpotassium, phenylpotassium, phenylsodium, phenyllithium, butyllithium and the like; magnesium alkyls and aryls such as diphenylmagnesium, diethylmagnesium, ethylmagnesium chloride, phenylmagnesium chloride, butylmagnesium bromide and the like; calcium, strontium and barium organo compounds such as barium alkyls and aryls; alkyls and aryls of Group IIb metals such as diethylzinc, diphenylzinc, ethylzinc chloride, diethylcadmium, dibutylcadmium and the like; Grignard agents such as phenylmagnesium bromide may also be employed. Mixtures of these compounds may be employed as the first or (A) catalyst component in the catalyst of this invention. It is usually preferred to employ organoaluminum compounds such as trialkylaluminums, dialkylaluminum halides, alkylaluminum dihalides and aluminum-sesquihalides.

The metal salts employed in the catalysts of this invention as the second or (B) catalyst component are selected from the salts of molybdenum and tungsten. Representatives of such salts include halides such as chlorides, bromides, iodides, and fluorides, which include compounds such as molybdenum pentachloride, tungsten hexachloride, molybdenum pentabromide, tungsten hexabromide, molybdenum pentaiodide, tungsten hexaiodide, molybdenum pentafluoride, molybdenum hexafluoride and tungsten hexafluoride. Other representative salts are those of acetylacetonates, sulphates, phosphates, nitrates and the like which include compounds such as molybdenum phosphate, tungsten phosphate, molybdenum nitrate, tungsten nitrate, molybdenum acetylacetonate, tungsten acetylacetonate, molybdenum sulphate, and tungsten sulphate. Mixtures of these salts may also be employed. Of these, it is usually preferred to employ tungsten halides and molybdenum halides representative of which are tungsten hexachloride and molybdenum pentachloride.

The third or (C) component of the catalyst system of this invention are compounds which respond to the formula R—Y—H wherein Y is selected from the group consisting of oxygen and sulfur and R is a radical selected from the group consisting of (1) hydrogen, (2) alkyl, (3) aryl, (4) arylalkyl, (5) alkaryl, (6) alkenyl, (7) when Y is S, R is thioalkyl, thioarylalkyl and thioalkaryl, (8) when Y is O, R is alkoxy, arylalkoxy and alkaryloxy and (9) radicals of (2) through (6) wherein at least one hydrogen of R is substituted by at least one hydroxyl (OH) or thiol (SH) group.

Thus, the formula above defines a number of types of compounds. It defines water (HOH), hydrogen sulfide (HSH), both saturated and unsaturated alcohols (ROH), mercaptans (RSH), hydroperoxides (ROOH), hydrodisulfides (RSSH), polyalcohols (HOROH), polymercaptans (HSRSH), and hydroxy mercaptans (HSROH) or thioalcohols (HORSH). Representative examples of the materials responding to the formula above are alcohols representative of which are methanol, ethanol, isopropanol, tertiarylbutyl alcohol, amyl alcohol, benzyl alcohol, allyl alcohol, 1,1-dimethyl benzyl alcohol, phenol, tertiarybutyl catechol, alpha and beta naphthyl alcohol; mercaptans such as methyl, ethyl propyl, isopropyl, butyl, amyl and similar mercaptans, allyl mercaptan, thiophenol, 4-methylthiophenol, 4-mercaptophenol; the hydroperoxides such as cumyl hydroperoxide, tertiarybutyl hydroperoxide; the hydrodisulfides such as cumyl hydrodisulfide, t-butyl hydrodisulfide; the polyalcohols such as ethylene glycol, glycerol, and similar polyglycols; catechol, resorcinol, hydroquinone, pyrogallol; the polymercaptans such as 1,3-propane dithiol, 1,4-dithiobenzene; the hydroxymercaptans or thioalcohols such as ethane-2-ol-1-thiol, 1-hydroxy-4-thiobenzene.

One of the unusual and distinguishing features of the catalyst system of this invention to convert the 8 carbon atom alicyclic compounds into the 16 carbon atom alicyclic compounds is that the compound of the formula R—Y—H, wherein R and Y have been previously defined, depending on the particular 8 carbon atom alicyclic compound employed, the particular organometallic compound and the particular Group IVb metal salt chosen and on the particular R—Y—H compound chosen, when employed in fairly substantial amounts, are known to reduce drastically the activity of the catalyst system by which the macrocyclization of this invention occurs. An unexpected high activity of the catalyst of the present invention was found when compounds of the R—Y—H type were employed in relatively small amounts and added according to the teachings set forth in the present specification and examples. Since the instant invention contemplates the use of organometallic compounds in combination with transition metal salts and various oxygen and sulfur-containing compounds, and since factors or considerations will influence the optimum range of the three catalyst components in relation to each other, the molar ratios of the three components which optimize the reaction conditions cannot be readily set forth. However, by following the teachings found in this application, those skilled in the art can readily determine the optimum molar ratio of the three catalyst components to each other. Obviously, if one employs the oxygen or sulfur-containing compound, or as is designated above, component C in relatively large amounts, the activity of the catalyst will be reduced considerably or even destroyed.

It has been found that good results are obtained in the practice of the first step of this invention when the molar relationship between the three catalyst components, A, B and C as previously defined, are within a molar ratio of B/C ranging from about 0.3/1 to at least about 20/1 and the molar ratio of A/B is within the range of about 0.5/1 to at least 15/1. More preferred ratios are B/C of 0.5/1 to 5/1 and A/B of 0.5/1 to 8/1. Still more preferred ratios are B/C of 1/1 to 2/1 and A/B of 0.75/1 to 5/1.

The catalysts employed in this invention are prepared by mixing the components by known techniques. Thus, the catalysts may be prepared by "preformed" or "in situ" techniques. By the "preformed" method the catalyst components are mixed together prior to exposure of any of the catalyst components to the unsaturated compound to be used in the macrocyclization reaction. In the "in situ" method the catalyst components are added separately to the unsaturated compound to be used in the macrocyclization reaction. The catalyst components may be mixed either as pure compounds or as suspensions or solutions in liquids which do not adversely affect catalyst activity or the olefin metathesis reaction. Representative of such liquids are saturated hydrocarbons such as hexane, pentane and the like or aromatics such as benzene, toluene and the like.

While the presence of the unsaturated precursor is not essential during the formation of active catalyst by a mixing of components A, B and C and this fact facilitates the use of "preformed" catalysts, it has been found that freshly preformed catalysts are generally more active than catalysts which have been allowed to age before use.

The order of addition of the three catalyst components to each other is of interest in the practice of this invention. There are various methods in which the three catalyst components can be brought into contact with the unsaturated precursor or unsaturated precursor/solvent mixture. The following is a numerical listing of these various methods in which A, B and C stand for the catalyst components as previously defined.

1. Simultaneous addition of A, B and C.
2. C followed by A and B which were previously preformed.
3. A and B preformed followed by C.
4. A followed by B and C which were preformed.
5. B and C preformed followed by A.
6. B followed by A and C which were preformed.
7. A and C preformed by followed by B.
8. A followed by B followed by C.
9. B followed by A followed by C.
10. C followed by B followed by A.
11. C followed by A followed by B.
12. B followed by C followed by A.
13. A followed by C followed by B.
14. Preformed A, B and C which was prepared by adding A to B and C preformed.
15. Preformed A, B and C which was prepared by adding B to A and C preformed.
16. Preformed A, B and C which was prepared by adding C to A and B preformed.

Of these various procedures, Procedures 6, 7, 11, 13 and 15 listed above are methods of preparation which reduce somewhat the catalyst activity. The remaining of the listed Procedures 1, 2, 3, 4, 5, 8, 9, 10, 12, 14 and 16 lead to the most active catalyst systems.

The amount of catalyst employed in the macrocyclization reaction of this invention may be varied over wide concentrations and has not been found to be critical. Of course, a catalytic amount of the catalyst must be employed. The optimum amount of catalyst depends upon a number of factors such as temperature, unsaturated precursors used, purity of precursors, reaction times desired and the like. Those skilled in the art will readily determine the optimum catalytic ranges. The macrocyclization can be conducted wherein the amount of catalyst employed is about 0.01 parts by weight of B per 100 parts by weight of unsaturated precursor employed, with components A and C adjusted to yield a desirable atomic ratio of A/B/C.

The practice of this invention is further illustrated by reference to the following examples which are intended to be representative rather than restrictive of the scope of the invention.

EXAMPLE I

A series of reactions was carried out whereby cyclooctene was coverted into a mixture of macrocyclics having the general formula $(C_nH_{14})_n$ by reacting cyclooctene in the presence of a catalyst comprising a mixture of tungsten hexachloride ($WCl_6$) and ethyl alcohol and ethyl aluminum dichloride (EADC). The $WCl_6$ was 0.05 molar in benzene. The ethanol was pre-reacted with $WCl_6$ in equal molar quantities. The EDAC was 0.20 molar in benzene. The various amounts and other relevent data are given in the talbe below. Each of the reactions was allowed to proceed 15 minutes and was then terminated by the introduction of the 2.0 ml benzene solution containing 0.03 gram of tetraethylene pentamine and 0.02 gram of di-ter-butyl-p-cresol and evaporated to dryness. The evaporated mixture was extracted three times with 50 ml portions of 1:1 volume ratio of isopropanol/hexene solvent system and a low molecular weight extractable portion thus isolated. These low molecular weight extractables are reported as macrocyclics in percent in the table below.

Parent mass spectroscopic analysis by low voltage mass spectroscopy was carried out and it was found that the extractable mixture was comprised of components possessing molecular weights according to the series: $220 + n \times 110 (n = 0, 1, 2, 3...)$. This corresponds to a dimer (when $n = 0$), a trimer (when $n = 1$), a tetramer (when $n = 2$), and so forth, of the repeating monomer unit of the original polyoctenamer, that is $-CH_2-CH=CH-CH_2-(CH_2)_4-$. The Nuclear Magnetic Resonance spectroscopic analysis (NMR) of the low molecular weight extractable portion indicates the presence of one vinylene double bond for every eight carbons, similar to cyclooctene and polyoctenamer, and possessing three types of hydrogens (A) vinylic: ($CH=CH$); (B) allylic: ($CH_2-CH=CH$); and (C) methylenic: ($CH_2$). The relative ratio of vinylic/allylic/methylenic types of hydrogens was found to be essentially 1/2/4. Methyl hydrogens: ($CH_3$) or terminal unsaturation type of hydrogens: ($CH=CH_2$) were not detected in the NMR spectrum.

Hence, the mass spectroscopy and NMR spectroscopy results reveal that the low molecular weight extractable portion consists of a mixture of macrocyclics of the general formula:

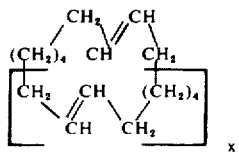

where $x = 1, 2, 3 \ldots$

For $x = 1$, the ring is of 16 carbons, 2 double bonds and has a molecular weight of 220. For $x = 2$, the ring is of 24 carbons, 3 double bonds and has a molecular weight of 330. For $x = 3$, the ring is of 32 carbons, 4 double bonds and has a molecular weight of 440. This series of molecular weights is consistent with the experimentally determined low voltage mass spectroscopy and the structure presented above is consistent with the NMR spectrum analysis.

| Reaction No. | Cyclo-octene (ml) | Benzene (ml) | $WCl_6/C_2H_5OH(1:1)$ (moles × 10⁴) | EADC (moles × 10⁴) | Macro-cyclics (%) |
|---|---|---|---|---|---|
| 1 | 5 | 95 | 0.5 | 2.0 | 46.2 |
| 2 | 4 | 96 | 0.5 | 2.0 | 48.5 |
| 3 | 3 | 97 | 0.5 | 2.0 | 73.2 |
| 4 | 2 | 98 | 0.5 | 2.0 | 91.4 |
| 5 | 1 | 99 | 0.5 | 2.0 | 98.3 |

These data illustrate that dilutions favor the formation of macrocyclics.

EXAMPLE II

A 1.75 ml sample of cyclooctene was dissolved in benzene to form a 50 ml solution. Under nitrogen atmosphere, 0.5 ml solution of $WCl_6/C_2H_5OH$ (1:1) in benzene of 0.05 molar concentration was added followed by 0.5 ml EADC of 0.2 molar concentration. The mixture was sampled at variable times and analyzed by gas chromatography using cyclooctane as an internal standard. The following table contains the observed data regarding the composition of the mixture with respect to conversion.

| Reaction No. | Conversion (%) | Remaining Cp (%) | Cyclic $C_{16}$ (%) | Cyclic $C_{24}$ (%) | Cyclic $C_{32}$ (%) | Other (%) |
|---|---|---|---|---|---|---|
| 1 | 47 | 53 | 11 | 6 | 1 | 29 |
| 2 | 77 | 23 | 18 | 9 | 3 | 47 |
| 3 | 88 | 12 | 22 | 15 | 5 | 46 |
| 4 | 90 | 10 | 19 | 13 | 5 | 53 |
| 5 | 91 | 9 | 20 | 12 | 7 | 52 |
| 6 | 93 | 7 | 18 | 12 | 6 | 57 |
| 7 | 95 | 5 | 20 | 12 | 4 | 59 |
| 8 | 97 | 3 | 19 | 12 | 5 | 61 |

The data demonstrates that is possible to convert cyclooctene to 1,9-cyclohexadecadiene with a selectivity of about 25%.

The macrocyclic compound 1,9-cyclohexadecadiene obtained from cyclooctene as indicated in Example 1 can be converted into $\Delta^8$ - cyclohexadecene-1-one (I), according to the equation

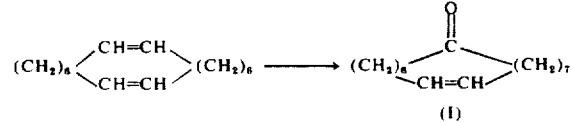

(I)

and also to the respective diketones:

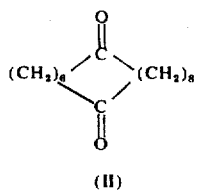 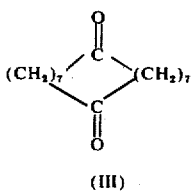

(II)                (III)

Processes available for the conversion of unsaturated double bonds into carbonyl functional groups are numerous. It is possible to convert the double bond first into a hydroxy group by well documented reactions such as:

1. addition of HX (X = Cl, Br, I) to the double bond to form the respective halogenated derivative of the $C_{16}$ macrocyclic, followed by hydrolysis to form the hydroxy substituted $C_{16}$ macrocyclic;

2. reaction of the unsaturated macrocyclic with concentrated $H_2SO_4$, forming the respective sulfate derivative of the $C_{16}$ macrocyclic, followed by hydrolysis to form the hydroxy substituted $C_{16}$ macrocyclic;

3. reaction of the unsaturated macrocyclic with $NaBH_4$ in the presence of $BF_3$.etherate catalyst according to the well-known hydroboration reaction, followed by the alkaline hydrolysis of the respective borane yielding the hydroxy substituted $C_{16}$ macrocyclic; all of these followed by oxidation of the hydroxy to a carbonyl.

The oxidation of the hydroxy substituted macrocyclic into the respective carbonyl can be carried out by several methods. It is possible to use various oxidation reagents such as $H_2O_2$, chromium trioxide, aluminum isopropoxide in acetone (Oppenauer reaction) and others. It is understood that any particular oxidation process requires appropriate solvent media, acidity and other specific conditions which should be employed in order to obtain optimum yields of the desired product. It is conveivable that the isolation step of the pure hydroxy substituted $C_{16}$ macrocyclic intermediate can be eliminated, as it is possible to conduct the oxidation step of the said intermediate directly on the crude material. The following example describes a conversion of the 1,9-cyclohexadecadiene into the respective ketones without isolation of the respective alcohols.

EXAMPLE III

Into a solution of 22.0 grams 1,9-cyclohexadecadiene in 50 milliliters of anhydrous tetrahydrofuran, containing 1.14 grams of sodium borohydride ($NaBH_4$), was slowly added 5.6 grams of boron trifluoride tetrahydrofuran complex ($BF_3$.THF) dissolved in 20 milliliters of tetrahydrofuran (THF) over a 2 hour period, maintaining a temperature of 30° C. The reaction mixture was then treated with 11.0 milliliters 3 molar of sodium hydroxide solution (NaOH), followed by a slow addition of 14.0 milliliters of 30 percent of hydrogen peroxide ($H_2O_2$) solution. The crude product was poured into 300 milliliters of water and extracted with pentane.

Analysis by gas chromatography indicated a total conversion of 71 percent of which 48 percent was $\Delta^8$-cyclohexadecene-1-one (I) and 23 percent mixture of the diketones (II) and (III).

The unsaturated $C_{16}$ macrocyclic 1,9-cyclohexadecadiene possesses two double bonds separated by six ($CH_2$) groups. Thus, in attempting to convert one double bond to a ketone functional group there is always a possibility of obtaining some diketones (II) and (III). By adjusting the reagent ratios employed it is possible to minimze or maximize the formation of diketones.

Methods of conversion of carbon-to-carbon double bonds to carbonyl functional groups, excluding the hydroxy intermediate may also be employed in the syntheses of compounds (I), (II) and (III), from 1,9-cyclohexadecadiene. A possible process which may be employed is the conversion of the double bond to an epoxide by peroxy acids such as: peroxybenzoic acid or peroxytrifluoroacetic acid, followed by isomerization to the carbonyl according to the formula:

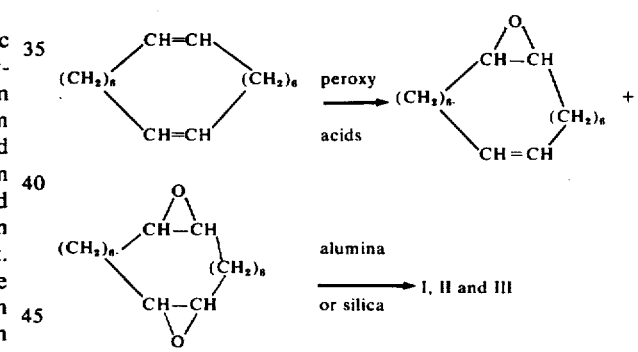

Another method will be the hydroboration of the $C_{16}$ macrocyclic diene and direct oxidation of the borane derivative:

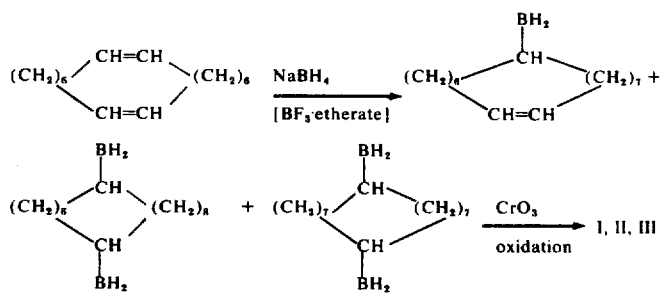

EXAMPLE IV

Hydroboration: a 500 ml 3-neck flask was fitted with a reflux condenser sealed with calcium sulfate (indicator Drierite), a nitrogen inlet tube and a dropping funnel containing 4 ml. (ca. 30 mmoles) of boron trifluoride etherate in 10 ml of diglyme. The flask contained 2.20 grams (10 mmoles) of 1,9-cyclohexadecadiene and 0.57 grams (15 mmoles) of sodium borohydride in 100 ml of diglyme. The $BF_3$ solution was added at a rate to maintain the temperature at 25°–45° C. (ca. 5 min.). The reaction mixture was heated at 80° C. for 2 hours as periodic samples were withdrawn and injected into the gas chromatograph. The organoborane was light yellow in color. The flask content was cooled and 30 ml of water added to destroy the excess hydride.

Oxidation: When the flask had cooled to room temperature, 200 ml of ethyl ether was added for mild oxidation conditions and ease of separation. A solution of 2.5 g (25 mmoles) of chromium trioxide and 5.0 g (50 mmoles) of sulfuric acid in 40 ml of water (ca. 8N) was added over a 10 minute period to maintain the temperature at 25°–35° C. The green chromic sulfate began to form upon addition of the oxidant. Refluxing was maintained for 3 hours. Three-hundred ml of water was added and the ether layer separated. The aqueous layer was extracted twice with 50 ml portions of ether and the extracts combined. Excess oxidant in the ether portion was destroyed with solid sodium bisulfite, and then washed with a sodium carbonate solution. The organic material was dried over calcium chloride and the solvents removed, ethyl ether at 25 mm and diglyme at 29°–31°C. at 2–3 mm. The mixture of products weighed slightly over 2 grams.

The products were isolated by gas chromatographic trapping methods. The cyclic ketones were identified by melting points as compared to literature values, mass spectrometry, nuclear magnetic resonance, infrared and elemental analysis. There was obtained about 26% by weight of $\Delta^8$-cyclohexadecene-1-one, 22% by weight of 1,9-diketocyclohexadecane, 19% by weight of cyclohexadecanone and 22% by weight of 1,8-diketocyclohexadecane While certain representative embodiments and details have been shown for the purpose of illustrating the invention, it will be apparent to those skilled in this art that various changes and modifications may be made therein without departing from the spirit or scope of the invention.

What is claimed is:

1. The method for the preparation of alicyclic ketones which contain 16 carbon atoms in the alicyclic ring which comprises subjecting an alicyclic compound corresponding to the formula:

wherein
1. Q comprises a sequence of six carbon atoms situated in linear succession between the methylidene carbons which constitute the double bond;
2. the carbon atoms in the linear succession of Q may be interconnected by both carbon-carbon single bonds and carbon-carbon double bonds;
3. any of the carbon atoms in the linear succession of Q may be substituted by alkyl radicals; and
4. said alicyclic compounds containing no conjugated double bonds, while said hydrocarbon is diluted to about 10% in an inert diluent to a catalyst comprising (A) at least one organometallic compound wherein the metal is selected from the group consisting of Ia, IIa, IIb and IIIa groups of the Periodic Table of Elements, the organo portion of said organometallic compound being selected from the group consisting of trialkyls, triaryls, dialkyl halides, alkyl dihalides, dialkyl hydrides, diaryl hydrides, aryl dihydrides and aryl halides; (B) at least one metal salt selected from the group consisting of molybdenum and tungsten halides, acetylacetonates, sulfates, phosphates and nitrates; and (C) at least one compound of the general formula R—Y—H wherein Y is selected from the group of oxygen and sulfur and wherein R is a radical selected from the group consisting of (1) hydrogen, (2) alkyl, (3) aryl, (4) arylalkyl, (5) alkaryl, (6) alkenyl, (7) when Y is S, R is thioalkyl, thioarylalkyl and thioalkaryl, (8) when Y is O, R is alkoxy, arylalkoxy and alkaryloxy and (9) radicals of (2) through (6) wherein at least one hydrogen of said radicals is substituted by a material selected from hydroxyl (OH) and thiol (SH) groups, wherein the molar relationship between catalyst component (A), (B) and (C) are within a molar ratio of B/C ranging from about 0.3/1 to at least about 20/1, and the molar ratio of A/B is within the range of about 0.5/1 to at least 15/1, to form at least one cyclic polyolefin corresponding to the formula:

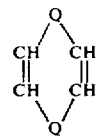

wherein
1. Q comprises a sequence of six carbon atoms situated in linear succession between the methylidene carbons which constitute the double bond;
2. the carbon atoms in the linear succession of Q may be interconnected by both carbon-carbon single bonds and carbon-carbon double bonds;
3. any of the carbon atoms in the linear succession of Q may be substituted by alkyl radicals; and
4. said alicyclic compounds containing no conjugated double bonds, and subsequently subjecting said cyclic polyolefin to a sequence of reactons whereby at least one and not more than two of the —CH═CH— groups are converted to a

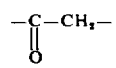

group to form a cyclic compound containing 16 carbon atoms in the alicyclic ring and containing one or two carbonyl functional groups.

2. The method for the preparation of alicyclic ketones which contain 16 carbon atoms in the alicyclic ring which comprises subjecting an alicyclic compound corresponding to the formula:

wherein
1. Q comprises a sequence of six carbon atoms situated in linear succession between the methylidene carbons which constitute the double bond;
2. the carbon atoms in the linear succession of Q may be interconnected by both carbon-carbon single bonds and carbon-carbon double bonds;
3. any of the carbon atoms in the linear succession of Q may be substituted by alkyl radicals; and
4. said alicyclic compounds containing no conjugated double bonds, while said hydrocarbon is diluted to about 10% in an inert diluent to a catalyst comprising (A) at least one organometallic compound
wherein the metal is selected from the group consisting of Ia, IIa, IIb and IIIa groups of the Periodic Table of Elements, said organometallic compounds having at least one metal-to-carbon bond; (B) at least one metal salt selected from the group consisting of molybdenum and tungsten, acetylacetonates, sulfates, phosphates and nitrates; and (C) at least one compound of the general formula R—Y—H wherein Y is selected from the group of oxygen and sulfur and wherein R is radical selected from the group consisting of (1) hydrogen, (2) alkyl, (3) aryl, (4) arylalkyl, (5) alkaryl, (6) alkenyl, (7) when Y is S, R is thioalkyl, thioarylalkyl and thioalkaryl, (8) when y is O, R is alkoxy, aralalkoxy and alkaryloxy and radicals of (2) through (6) wherein at least one hydrogen is substituted by a material selected from hydroxyl (OH) and thiol (SH) groups to form at least one material corresponding to the formula:

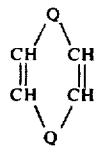

in which Q is selected from the group consisting of —(CH$_2$)$_6$— and —(CH$_2$)$_2$— CH=CH—(CH$_2$)$_2$— and subsequently converting at least one of the double bonds into a carbonyl functional group, wherein the molar relationship between catalyst components (A), (B) and (C) are within a molar ration of B/C ranging from about 0.3/1 to at least about 20/1, and the molar ratio, or A/B is within the range of about 0.5/1 to at least 15/1.

3. The method for the preparation of alicyclic ketones which contain 16 carbon atoms in the alicyclic ring which comprises subjecting:

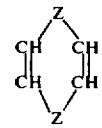

in which Z is selected from the group consisting of —(CH$_2$)$_6$— and —(CH$_2$)$_2$—CH=CG—(CH$_2$)$_2$13 to a sequence of reactions whereby at least one of the —CH=CH— groups is converted to a

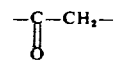

group

4. The method according to claim 3 wherein any hydrogen in the —(CH$_2$)$_6$— —(CH$_2$)$_2$—CH=CH—(CH$_2$)$_2$— groups is substituted by an alkyl group.

* * * * *